US008675914B2

(12) United States Patent
Wang et al.

(10) Patent No.: US 8,675,914 B2
(45) Date of Patent: Mar. 18, 2014

(54) METHOD AND SYSTEM FOR NEEDLE TRACKING IN FLUOROSCOPIC IMAGE SEQUENCES

(75) Inventors: Peng Wang, Princeton, NJ (US); Marcus Pfister, Bubenreuth (DE); Terrence Chen, Princeton, NJ (US); Martin Ostermeier, Buckenhof (DE); Dorin Comaniciu, Princeton Junction, NJ (US)

(73) Assignee: Siemens Aktiengesellschaft, München (DE)

( * ) Notice: Subject to any disclaimer, the term of this patent is extended or adjusted under 35 U.S.C. 154(b) by 506 days.

(21) Appl. No.: 12/880,319

(22) Filed: Sep. 13, 2010

(65) Prior Publication Data

US 2011/0064189 A1 Mar. 17, 2011

Related U.S. Application Data

(60) Provisional application No. 61/242,078, filed on Sep. 14, 2009.

(51) Int. Cl.
*G06K 9/00* (2006.01)

(52) U.S. Cl.
USPC ........... 382/103; 382/107; 382/128; 382/132; 382/173; 600/424; 378/4; 378/42; 378/62

(58) Field of Classification Search
None
See application file for complete search history.

(56) References Cited

U.S. PATENT DOCUMENTS

| | | | |
|---|---|---|---|
| 6,055,449 A * | 4/2000 | Navab | 600/427 |
| 6,764,449 B2 | 7/2004 | Lee et al. | |
| 6,778,689 B1 | 8/2004 | Aksit et al. | |
| 7,359,746 B2 | 4/2008 | Arata | |
| 2002/0058868 A1 | 5/2002 | Hoshino et al. | |
| 2003/0065260 A1* | 4/2003 | Cheng et al. | 600/427 |
| 2006/0058633 A1 | 3/2006 | Hoshino et al. | |
| 2006/0058643 A1 | 3/2006 | Florent et al. | |
| 2006/0133567 A1* | 6/2006 | Florent et al. | 378/62 |
| 2007/0118100 A1* | 5/2007 | Mahesh et al. | 606/32 |
| 2007/0189580 A1 | 8/2007 | Slabaugh et al. | |
| 2007/0270692 A1 | 11/2007 | Barbu et al. | |
| 2008/0025588 A1* | 1/2008 | Zhang et al. | 382/130 |
| 2008/0247621 A1 | 10/2008 | Zarkh et al. | |
| 2008/0275335 A1* | 11/2008 | Zhang et al. | 600/424 |
| 2010/0121181 A1 | 5/2010 | Wang et al. | |

OTHER PUBLICATIONS

Wang et al., Robust guidewire tracking in fluoroscopy, Jun. 20-25, 2009, IEEE: Computer Vision and Pattern Recognition, CVPR 2009.*

Barbu, A. et al., "Hierarchical Learning of Curves Application to Guidewire Localization in Fluoroscopy", in (CVPR), 2007.

Mazouer, P. et al., "User-Constrained Guidewire Localization in Fluoroscopy", in (Medical Imaging: Image Processing), Proc. SPIE, 2009.

* cited by examiner

*Primary Examiner* — Matthew Bella
*Assistant Examiner* — Jason Heidemann
(74) *Attorney, Agent, or Firm* — Michele L. Conover

(57) ABSTRACT

A method and system for tracking a needle in a fluoroscopic image sequence is disclosed. In order to track a needle in a fluoroscopic image sequence, the needle is initialized in a first frame of the fluoroscopic image sequence. Needle segments are detected in each subsequent frame of the fluoroscopic image sequence, and the needle is detected in each frame of the fluoroscopic image by tracking the needle from a previous frame of the fluoroscopic image sequence based on the detected needle segments in the current frame.

25 Claims, 4 Drawing Sheets

METHOD AND SYSTEM FOR NEEDLE TRACKING IN FLUOROSCOPIC IMAGE SEQUENCES

This application claims the benefit of U.S. Provisional Application No. 61/242,078, filed Sep. 14, 2009, the disclosure of which is herein incorporated by reference.

BACKGROUND OF THE INVENTION

The present invention relates to x-ray imaging, and more particularly, to needle tracking in 2D fluoroscopic image sequences.

In image guided abdominal interventions, needle tracking has important applications. Needle tracking provides the positions of needles in fluoroscopic images of the abdomen. Needle tracking can be used to compensate for breathing motion in fluoroscopic image sequences and to guide real-time overlaying of 3D images, which are acquired prior to an intervention. Needle detection and tracking in fluoroscopic image sequences is challenging due to the low signal to noise ratio of the fluoroscopic images, as well as the need for real-time speed and a high level of accuracy. Furthermore, different types of needles typically show a large variation in shape and appearance in fluoroscopic images, thus increasing the difficulty of implementing automatic needle tracking.

Since a needle is essentially a one-dimensional thin structure, tracking methods that use regional features, such as holistic intensity, textures, and color histograms, cannot track a needle well in fluoroscopic images. Active contour and level set based methods rely heavily on intensity edges, so they are easily attracted to image noise in fluoroscopic images. Considering the noise level in typical fluoroscopic images, conventional methods cannot deliver the desired speed, accuracy, and robustness for abdominal interventions. Accordingly, a robust, efficient, and accurate method of needle tracking is desirable.

BRIEF SUMMARY OF THE INVENTION

The present invention provides a method and system for needle tracking in fluoroscopic image sequences. Embodiments of the present invention provide a hierarchical framework to continuously and robustly track a needle for image-guided interventions. Embodiments of the present invention can be used to track the motion of a needle for breathing motion compensation in abdominal interventions.

In one embodiment of the present invention, needle segments are detected in a plurality of frames of the fluoroscopic image sequence. The needle in a current frame of the fluoroscopic image sequence is then detected by tracking the needle from a previous frame of the fluoroscopic image sequence based on the needle position in the previous frame and the detected needle segments in the current frame. The needle can be initialized in a first frame of the fluoroscopic image sequence, for example, using an interactive needle detection method.

These and other advantages of the invention will be apparent to those of ordinary skill in the art by reference to the following detailed description and the accompanying drawings.

DETAILED DESCRIPTION

The present invention relates to a method and system for needle tracking in fluoroscopic image sequences. Embodiments of the present invention are described herein to give a visual understanding of the needle tracking method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a framework for detecting and tracking a needle for breathing motion compensation in abdominal interventions. In this framework, an interactive needle detection method can be used to initialize the needle position and shape at the beginning of an intervention. At the acquisition of subsequent images, the needle is continuously tracked, and the positions of the needle in the frames of a fluoroscopic image sequence are output and used for breathing motion compensation in the intervention. Embodiments of the present invention utilize a hierarchical framework, in which at each frame, an offline learned (trained) needle segment detector automatically identifies small segments of a needle and provides primitive features for subsequent tracking. Based on the identified segments an affine tracking method robustly tracks the needle motion across successive frames.

Figure 1:
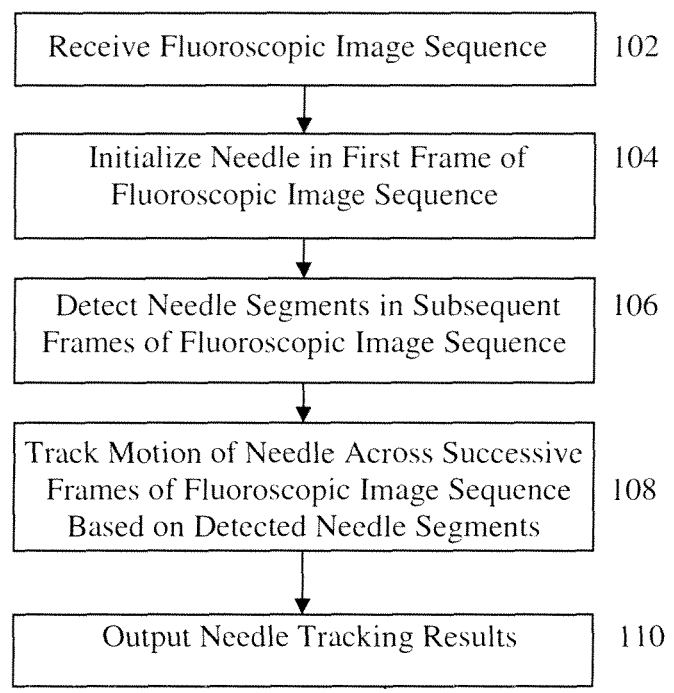
FIG. 1 illustrates a method for tracking a needle in a fluoroscopic image sequence according to an embodiment of the present invention.

FIG. 1 illustrates a method for tracking a needle in a fluoroscopic image sequence according to an embodiment of the present invention. The method of FIG. 1 transforms image data representing human anatomy, such as an abdominal cavity, in order to track a needle in the abdominal cavity by generating images showing the needle in the frames of an image sequence. As illustrated in FIG. 1, at step 102, a fluoroscopic image sequence is received. The fluoroscopic image sequence can be a sequence of low dose 2D fluoroscopic (x-ray) images taken over a period of time. Each image in the fluoroscopic image sequence is referred to herein as a "frame". The fluoroscopic image sequence can be received directly from an x-ray imaging device that captured the images. For example, the fluoroscopic image sequence can be received from an x-ray imaging device in real time as the fluoroscopic images are captured by the x-ray imaging device. It is also possible that the fluoroscopic image sequence is received by loading a previously generated fluoroscopic image sequence from a computer readable medium, or memory or storage of a computer system.

At step 104, a needle is initialized in a first frame of the fluoroscopic image sequence. As used herein, the term "first frame" refers to any frame in a sequence of fluoroscopic images at which the needle tracking process is initialized. According to an exemplary embodiment, in order to ensure accuracy and robustness during interventions, an interactive needle detection method can be used to initialize the needle in the first frame of the fluoroscopic image sequence. The interactive needle detection can detect the needle in the frame in response to user inputs to constrain a search for the needle. For example, a user may select two points in the frame, each one at or near one end of the needle. The user can select the points by clicking on the points with a user input device, such as a mouse. If the initial needle detected based on the two points selected by the user is not satisfactory, additional points may be selected by the user to further constrain the needle detection method in order to obtain refined detection results. Such an interactive detection method is described in greater detail in Mazouer et al., "User-Constrained Guidewire Localization in Fluoroscopy," *Medical Imaging* 2009: *Physics of Medical Imaging*, Proc. SPIE (2009), Volume 7258 (2009), pp. 72561K-72591K-9 (2009), which is incorporated herein by reference. Although an interactive needle detection method is described above, the present invention is not limited thereto and a fully automatic needle detection method or fully manual needle detection may also be used to initialize the needle in the first frame of the fluoroscopic image sequence.

Figure 2:
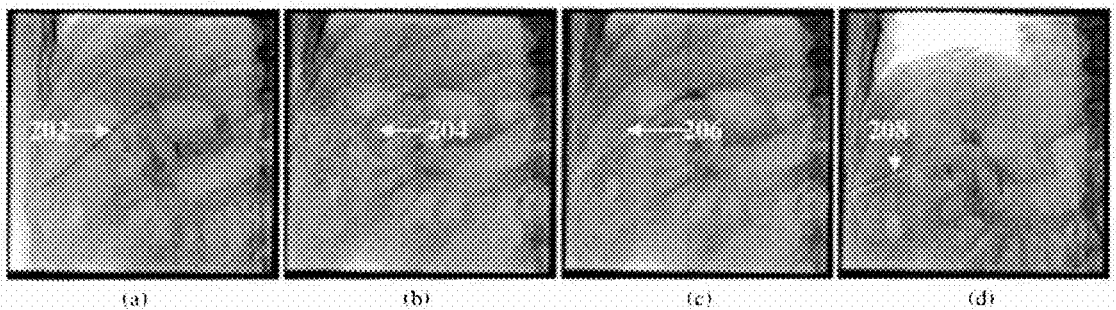
FIG. 2 illustrates exemplary needle tracking results resulting from various steps of the method of FIG. 1.

FIG. 2 illustrates exemplary needle tracking results resulting from various steps of the method of FIG. 1. Image (a) of FIG. 2 shows an initialized needle 202 in a first frame of an exemplary frame fluoroscopic image sequence.

Returning to FIG. 1, at step 106, needle segments are detected in each subsequent frame in the fluoroscopic image sequence. That is, needle segments are detected in each frame of the fluoroscopic image sequence after the first frame in which the needle is initialized. According to an advantageous embodiment, learning based needle segment detection is used to independently detect segments of the needle in each subsequent frame of the fluoroscopic image sequence. The detected needle segments in the frames of the fluoroscopic image sequence are used as primitives for affine needle tracking in step 108.

The appearance of a needle is difficult to distinguish in a fluoroscopic image due to the low signal to noise ratio. Traditional edge detectors and ridge detectors will produce many false detections while missing thin needle parts. According to an embodiment of the present invention, a learning based needle segment detection method is used. This learning based needle segment detection method utilizes needle segment detector that is trained offline using training data to detect needle segments in each frame of the fluoroscopic image sequence. Such a trained needle segment detector can identify weak needle segments in low quality fluoroscopic images.

According to an advantageous embodiment, the learning based needle detection method uses a probabilistic boosting tree (PBT) to train a needle segment detector based on annotated training data. PBT is a supervised method extended from the well-known AdaBoost algorithm, which combines weak classifiers into a strong classifier. PBT further extends AdaBoost into a tree structure and is able to model complex distributions of objects, which is desirable in handling different types of needles in fluoroscopy. According to an advantageous implementation, Haar features are extracted from images as the features used in the PBT classifier. Haar features measure image differences of many configurations and are fast to compute. In order to train the needle segment detector, numerous needles are annotated in training fluoroscopic images. Segments of the needles are cropped as positive training samples and image patches outside the needles are used as negative training samples. The training samples are then used to train the PBT based needle segment detector offline.

During online needle segment detection of an input image, such as a frame of the received fluoroscopic image sequence, the trained needle segment detector can identify if a patch of the image belongs to a needle or the background. The output of the PBT-based needle segment detector, denoted as P(x) given an image patch at the position x, is a combination of outputs from a collection of learned weak classifiers $H_k(x)$ with associated weights $\alpha_k$. The numeric output can be further interpreted as probabilistic measurements of needle segments, as expressed in Equation (1):

$$f(x) = \sum_k \alpha_k H_k(x) \qquad (1)$$

$$P(x) \propto \frac{e^{f(x)}}{e^{-f(x)} + e^{f(x)}}.$$

An image patch at the position x can be classified as a needle segment if P(x) is greater than a threshold (e.g., P(x)>0.5), and classified as background if P(x) is not greater than the threshold. As illustrated in FIG. 2, image (b) shows needle segments 204 detected by the trained needle segment detector in a frame of an exemplary fluoroscopic image sequence.

Returning to FIG. 1, at step 108, the needle is tracked across successive frames of the fluoroscopic image sequence based on the detected needle segments. This needle tracking searches for the motion of the needle between two successive frames using the detected needle segments as primitive features. For a current frame, the needle is detected by affine tracking the detected needle from a previous frame based on the needle position in the previous frame and the detected needle segments in the current frame. As used herein, the term "current frame" may be any frame in a fluoroscopic image sequence for which a needle is being detected.

By using the detected needle segments as primitive features, a coarse-to-fine affine tracking method is utilized to detect a needle candidate with maximum posterior probability. This coarse-to-fine tracking is based on a variable bandwidth kernel-based density smoothing method, which provides effective and efficient needle tracking results.

The needle tracking is formalized in a probabilistic inference framework to maximize the posterior probability of a tracked needle given the fluoroscopic images. In this framework, a needle hypothesis at the t-th frame is deformed from a previous frame. The needle hypothesis a the t-th frame is denoted as $\Gamma_t(x;u)$:

$$\Gamma_t(x;u) = T(\Gamma_{t-1}(x), u_x), \qquad (2)$$

where T is a needle shape transformation function and $u_x$ is the motion parameter. $\Gamma_{t-1}(x)$ is a tracked (detected) needle at a previous frame, which acts as a template for tracking the needle at the t-th frame. For simplicity of notation, a needle candidate is denoted hereinafter as $\Gamma_t(x)$. The posterior probability $P(\Gamma_t(x)|Z_t)$ can be expressed as:

$$P(\Gamma_t(x)|Z_t) \propto P(\Gamma_t(x))P(Z_t|\Gamma_t(x)). \qquad (3)$$

The tracked needle $\hat{\Gamma}_t(x)$ is estimated as the needle candidate that maximizes the posterior probability, i.e., $$\hat{\Gamma}_t(x) = \underset{\Gamma_t(x)}{\mathrm{argmax}} P(\Gamma_t(x)|Z_t).$$

In equation (3), $P(\Gamma_t(x))$ is a prior probability, which can be propagated from previous tracking results. The prior probability can be modeled as:

$$P(\Gamma_t(x)) = \frac{1}{\sqrt{2\pi}\,\sigma_\Gamma} \exp\left(\frac{-|D(\Gamma_t(x), \Gamma_{t-1}(x))|^2}{2\sigma_\Gamma^2}\right) \quad (4)$$

where $D(\Gamma_t(x),\Gamma_{t-1}(x))$ is the average of the shortest distances from points on candidate $\Gamma_t(x)$ to the shape template $\Gamma_{t-1}(x)$. A large kernel size $\sigma_\Gamma$ can be selected to allow large needle movements between frames. The likelihood measurement model $P(Z_t|\Gamma_t(x))$, is another component that plays a crucial role in achieving robust tracking results. Given a needle represented by N points $\Gamma_t(x)=\{x_1, x_2, \ldots, x_N\}$ that are interpolated from control points, the needle $\Gamma_t(x)$ is in an N-dimensional space, which makes the measurement model $P(Z_t|\Gamma_t(x))$ difficult to represent. In order to simplify the model, measurement independency can be assumed along a needle, i.e., $P(Z_t|x_i,\Gamma_t(x))=P(Z_t|x_i)$. Using this assumption, the measurement model $P(Z_t|\Gamma_t(x))$ can be decomposed into measurements as individual needle points, expressed as:

$$P(Z_t | \Gamma_t(x)) = \sum_{x_t} P(Z_t | x_i) P(x_i | \Gamma_t(x)), \quad (5)$$

where $P(Z_t|x_i)$ is the measurements at individual points on a needle, and $P(x_i|\Gamma_t(x))$ is the weights of individual points on the needle. According to an advantageous implementation, such weights can be set as equal to each other.

Embodiments of the present invention utilize multi-resolution affine tracking, which is based on a kernel-based smoothing method. In order to obtain measurements at each point x in a frame is computationally expensive and is prone to measurement noise at individual points. For example, measurements at points that are classified by the PBT-based needle segment detector as non-needle segments may not be reliable. The measurements can be made more robust and more efficient to compute by using kernel-based estimation (or smoothing). In the kernel-based estimation, measurements are made at a set of sampled locations $x_j^s$, of an entire image. In an advantageous implementation, the sampled locations $x_j^s$ are the points in a frame classified a needle segments by the trained needle segment detector. Based on Markov conditional independence, it can be assumed that observations at sampling points $x_j^s$ are independent of un-sampled points $x_i$, i.e., $P(Z_t|x_i,x_j^s)=P(Z_t|x_j^s)$. Therefore, the kernel-based measurement estimation can be expressed as:

$$P(Z_t | x_i) = \sum_j P(Z_t | x_j^s) G_\sigma(x_j^s, x_i), \quad (6)$$

where $P(x_j^s|x_i)=G_\sigma(x_j^s,x_i)$ is a Gaussian kernel with a bandwidth $\sigma$. The kernel-based measurement estimation can obtain smooth measurements in a neighborhood, reduce computations necessary to calculate the measurements, and allow for multi-resolution tracking Affine tracking recovers the motion of the needle between two successive frames, i.e., $u_x=u=(c,r,\theta,s_c,s_r)$, where c, r, and $\theta$ are translation and rotation parameters, and $s_c$ and $s_r$ scale factors in two directions. The affine tracking is formulated determining motion parameters to maximizing the posterior probability, i.e., maximizing E(u), as expressed below:

$$E(u) = P(\Gamma_t(x)) \sum_{x_t} P(x_i | \Gamma_t(x; u)) P(Z_t | x_i). \quad (7)$$

Tracking the affine motion can be efficiently implemented using variable bandwidths in kernel-based measurement smoothing. For example, translation searching can be performed at multiple resolutions for each frame, with decreased intervals $\{d_1 > d_2 > \ldots > d_T\}$. During the multi-resolution tracking, the corresponding bandwidth in equation (6) varies accordingly and can be denoted as $\sigma_i$. Incrementally decreasing bandwidth $\sigma_i$ leads to a coarse-to-fine tracking scheme. For example, to search the translation of a needle, a larger kernel bandwidth $\sigma_i$ is used at coarse resolutions to avoid missing tracking caused by larger sampling intervals. At fine resolutions, a smaller kernel bandwidth is used to obtain finer tracking results. Rotation and scale searches are performed using the multi-resolution manner similar to the translation. At coarse resolutions, the method searches a large range of rotation and scaling of a needle, and uses a larger bandwidth $\sigma_i$. At fine resolutions, a small range of rotation and scaling is searched with a small bandwidth. In this method, the translation, rotation and scaling factors are searched simultaneously. The kernel bandwidth in Eqn. (6) is set as proportional to the sampling intervals, so the tracking results automatically adapt to different resolutions.

As illustrated in FIG. 2, images (c) and (d) show needles 206 and 208, respectively, detected using multi-resolution affine tracking in exemplary frames of a fluoroscopic image sequence.

Returning to FIG. 1, at step 110, the needle tracking results for the fluoroscopic image sequence are output. For example, the needle tracking results can be output by displaying the fluoroscopic images in the sequence showing the tracked needle in each image, or by visualizing segmented organ images that moves with the tracked needles. Furthermore, the needle tracking results can be output by outputting the motion parameters determined for tracking the needle in successive frames of the fluoroscopic image sequence. The motion of the needle in the frames of the fluoroscopic image sequence can be due to breathing motion in the body of a patient. Accordingly, the determined motion parameters can be used to compensate for breathing motion in an abdominal intervention.

Figure 3:
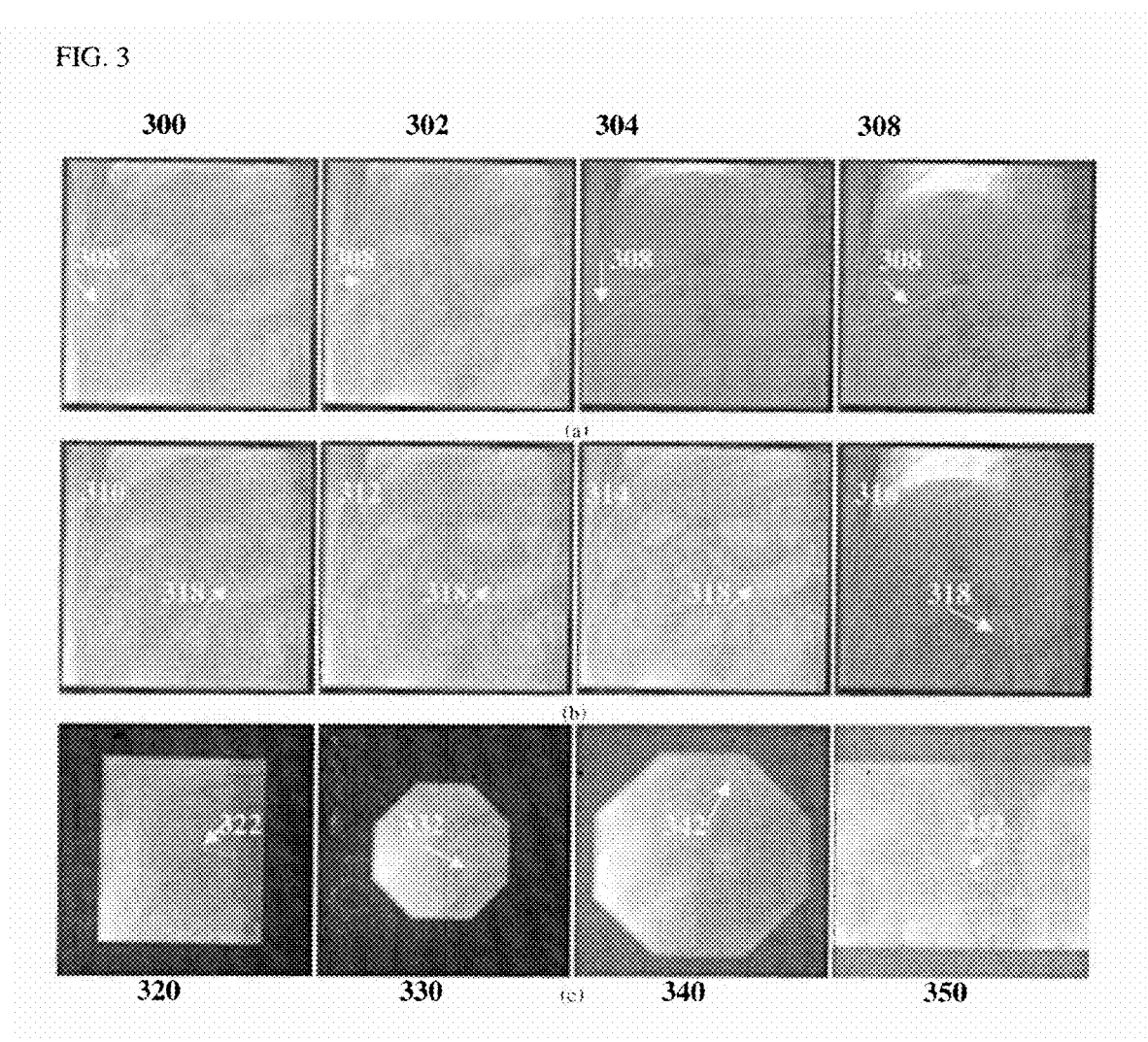
FIG. 3 illustrates exemplary needle tracking results generated using the method of FIG. 1.

FIG. 3 illustrates exemplary needle tracking results generated using the method of FIG. 1. As illustrated in FIG. 3, sequence (a) and sequence (b) show the same partial fluoroscopic image sequence with different needle initializations. In sequence (a), image 300 is the first frame of the sequence and needle 308 is initialized in image 300. Images 302, 304, and 306 are frames showing the tracked needle 608. In sequence (b), image 310 is the first frame of the sequence and needle 318 is initialized in image 310. Images 312, 314, and 316 are frames showing the tracked needle 318. In (c), images 320, 330, 340, and 350 show needle tracking results 322, 332, 342, and 352, respectively.

Figure 4:
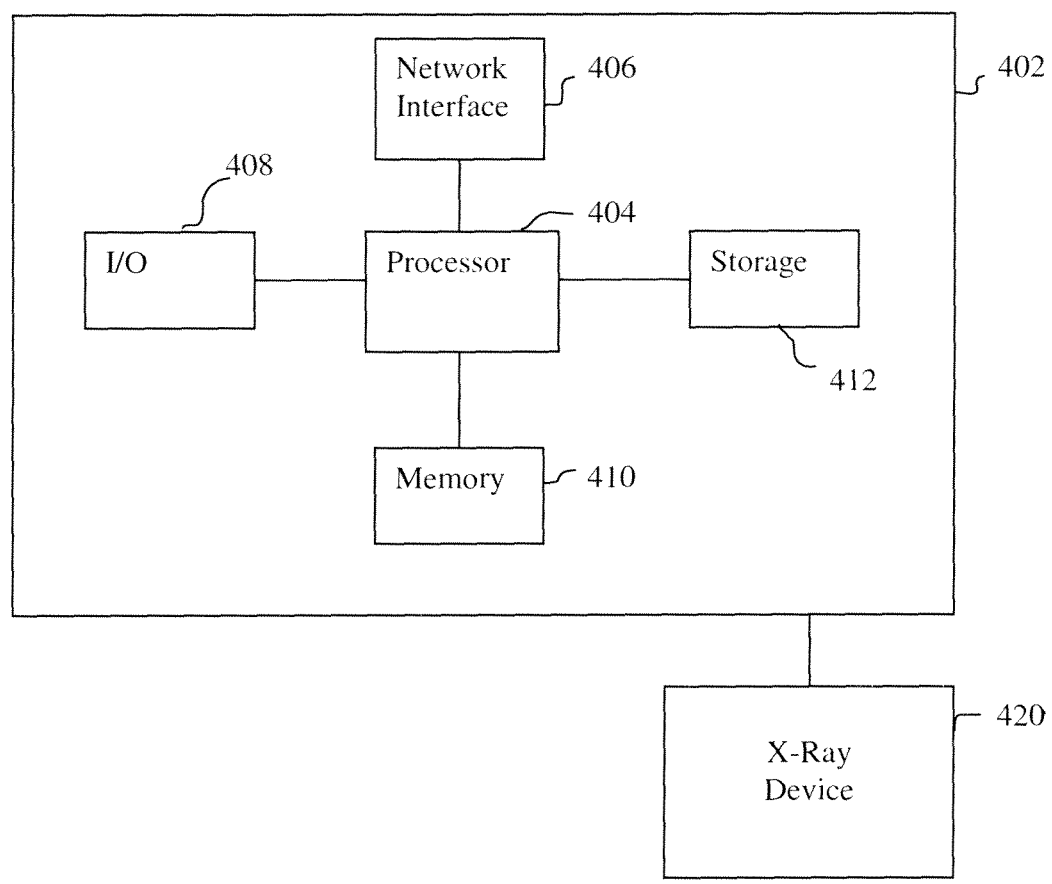
FIG. 4 is a high level block diagram of a computer capable of implementing the present invention.

The above-described methods for needle tracking in fluoroscopic image sequences may be implemented on a computer using well-known computer processors, memory units, storage devices, computer software, and other components. A high level block diagram of such a computer is illustrated in FIG. 4. Computer 402 contains a processor 404 which controls the overall operation of the computer 402 by executing computer program instructions which define such operation. The computer program instructions may be stored in a storage device 412, or other computer readable medium, (e.g., magnetic disk) and loaded into memory 410 when execution of the computer program instructions is desired. Thus, all method steps described above, including the method steps illustrated in FIG. 1, may be defined by the computer program instructions stored in the memory 410 and/or storage 412 and controlled by the processor 404 executing the computer program instructions. An image acquisition device 420, such as an X-ray imaging device, can be connected to the computer 402 to input fluoroscopic image sequences to the computer 402. It is possible to implement the image acquisition device 420 and the computer 402 as one device. It is also possible that the image acquisition device 420 and the computer 402 communicate wirelessly through a network. The computer 402 also includes one or more network interfaces 406 for communicating with other devices via a network. The computer 402 also includes other input/output devices 408 that enable user interaction with the computer 402 (e.g., display, keyboard, mouse, speakers, buttons, etc.) One skilled in the art will recognize that an implementation of an actual computer could contain other components as well, and that FIG. 4 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for tracking a needle in a fluoroscopic image sequence of at least at least a portion of a body of a patient, comprising:
    independently detecting needle segments in each of a plurality of frames of the fluoroscopic image sequence; and
    detecting the needle in a current frame of the fluoroscopic image sequence by tracking the detected needle from a previous frame of the fluoroscopic image sequence based on a position of the needle in the previous frame and the detected needle segments in the current frame, wherein the detected needle segments are used as primitive features to detect motion between the needle in the previous frame and the needle in the current frame due to breathing motion in the body of the patient.

2. The method of claim 1, further comprising:
    initializing the needle in a first frame of the fluoroscopic image sequence, wherein the plurality of frames are subsequent to the first frame in the fluoroscopic image sequence.

3. The method of claim 2, wherein said step of initializing a needle in a first frame of the fluoroscopic image sequence comprises:
    receiving at least two user inputs corresponding to locations of two end points of the needle in the first frame; and
    detecting the needled in the first frame based on the at least two user inputs.

4. The method of claim 1, wherein said step of independently detecting needle segments in each of a plurality of frames of the fluoroscopic image sequence comprises:
    detecting needle segments in each of the plurality of frames using a learning-based needle segment detector.

5. The method of claim 4, wherein said learning based needle segment detector is trained using a probabilistic boosting tree (PBT) and Haar features.

6. The method of claim 1, wherein said step of detecting the needle in a current frame of the fluoroscopic image sequence by tracking the detected needle from a previous frame of the fluoroscopic image sequence comprises:
    determining motion parameters corresponding to the motion between the needle in the previous frame and the needle in the current frame due to the breathing motion in the body of the patient.

7. The method of claim 6, wherein said step of determining motion parameters corresponding to the motion between the needle in the previous frame and the needle in the current frame due to the breathing motion in the body of the patient comprises:
    calculating the motion parameters using multi-resolution affine tracking of the needle from the previous frame to the current frame.

8. The method of claim 7, wherein the multi-resolution affine tracking uses kernel-based estimation based on the detected needle segments in the current frame.

9. The method of claim 6, further comprising:
    compensating for the breathing motion in an abdominal intervention based on the determined motion parameters.

10. The method of claim 1, further comprising:
    repeating said step of detecting the needle in a current frame of the fluoroscopic image sequence for each of the plurality of frames of the fluoroscopic image sequence.

11. An apparatus for tracking a needle in a fluoroscopic image sequence of at least at least a portion of a body of a patient, comprising:
    means for independently detecting needle segments in each of a plurality of frames of the fluoroscopic image sequence; and
    means for detecting the needle in a current frame of the fluoroscopic image sequence by tracking the detected needle from a previous frame of the fluoroscopic image sequence based on a position of the needle in the previous frame and the detected needle segments in the current frame, wherein the detected needle segments are used as primitive features to detect motion between the needle in the previous frame and the needle in the current frame due to breathing motion in the body of the patient.

12. The apparatus of claim 11, further comprising:
    means for initializing the needle in a first frame of the fluoroscopic image sequence, wherein the plurality of frames are subsequent to the first frame in the fluoroscopic image sequence.

13. The apparatus of claim 12, wherein said means for initializing a needle in a first frame of the fluoroscopic image sequence comprises:
    means for receiving at least two user inputs corresponding to locations of two end points of the needle in the first frame; and
    means for detecting the needled in the first frame based on the at least two user inputs.

14. The apparatus of claim 11, wherein said means for independently detecting needle segments in each of a plurality of frames of the fluoroscopic image sequence comprises:
    means for detecting needle segments in each of the plurality of frames using a learning-based needle segment detector.

15. The apparatus of claim 11, wherein said means for detecting the needle in a current frame of the fluoroscopic image sequence by tracking the detected needle from a previous frame of the fluoroscopic image sequence comprises:
    means for determining motion parameters corresponding to the motion between the needle in the previous frame and the needle in the current frame due to the breathing motion in the body of the patient.

16. The apparatus of claim 15, wherein said means for determining motion parameters corresponding to the motion between the needle in the previous frame and the needle in the current frame due to the breathing motion in the body of the patient comprises:
    means for calculating the motion parameters using multi-resolution affine tracking of the needle from the previous frame to the current frame.

17. The apparatus of claim 16, wherein the multi-resolution affine tracking uses kernel-based estimation based on the detected needle segments in the current frame.

18. A non-transitory computer readable medium encoded with computer executable instructions for tracking a needle in a fluoroscopic image sequence of at least at least a portion of a body of a patient, the computer executable instructions defining steps comprising:
    independently detecting needle segments in each of a plurality of frames of the fluoroscopic image sequence; and
    detecting the needle in a current frame of the fluoroscopic image sequence by tracking the detected needle from a previous frame of the fluoroscopic image sequence based on a position of the needle in the previous frame and the detected needle segments in the current frame, wherein the detected needle segments are used as primitive features to detect motion between the needle in the previous frame and the needle in the current frame due to breathing motion in the body of the patient.

19. The computer readable medium of claim 18, further comprising computer executable instructions defining the step of:
    initializing the needle in a first frame of the fluoroscopic image sequence, wherein the plurality of frames are subsequent to the first frame in the fluoroscopic image sequence.

20. The computer readable medium of claim 19, wherein the computer executable instructions defining the step of initializing a needle in a first frame of the fluoroscopic image sequence comprise computer executable instructions defining the steps of:

receiving at least two user inputs corresponding to locations of two end points of the needle in the first frame; and
    detecting the needled in the first frame based on the at least two user inputs.

21. The computer readable medium of claim 18, wherein the computer executable instructions defining the step of independently detecting needle segments in each of a plurality of frames of the fluoroscopic image sequence comprise computer executable instructions defining the step of:
    detecting needle segments in each of the plurality of frames using a learning-based needle segment detector.

22. The computer readable medium of claim 18, wherein the computer executable instructions defining the step of detecting the needle in a current frame of the fluoroscopic image sequence by tracking the detected needle from a previous frame of the fluoroscopic image sequence comprise computer executable instructions defining the step of:
    determining motion parameters corresponding to the motion between the needle in the previous frame and the needle in the current frame due to the breathing motion in the body of the patient.

23. The computer readable medium of claim 22, wherein the computer executable instructions defining the step of determining motion parameters corresponding to the motion between the needle in the previous frame and the needle in the current frame due to the breathing motion in the body of the patient comprise computer executable instructions defining the step of:
    calculating the motion parameters using multi-resolution affine tracking of the needle from the previous frame to the current frame.

24. The computer readable medium of claim 23, wherein the multi-resolution affine tracking uses kernel-based estimation based on the detected needle segments in the current frame.

25. The computer readable medium of claim 18, further comprising computer executable instructions defining the step of:
    repeating said step of detecting the needle in a current frame of the fluoroscopic image sequence for each of the plurality of frames of the fluoroscopic image sequence.

* * * * *